United States Patent
Chen et al.

(10) Patent No.: US 11,419,905 B2
(45) Date of Patent: Aug. 23, 2022

(54) BACTEROIDES OVATUS FOR RELIEVING ENDOTOXIN INFECTION AND APPLICATION THEREOF

(71) Applicant: Jiangnan University, Wuxi (CN)

(72) Inventors: Wei Chen, Wuxi (CN); Qixiao Zhai, Wuxi (CN); Huizi Tan, Wuxi (CN); Wenwei Lu, Wuxi (CN); Fengwei Tian, Wuxi (CN); Jianxin Zhao, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/082,594

(22) Filed: Oct. 28, 2020

(65) Prior Publication Data

US 2021/0060091 A1     Mar. 4, 2021

Related U.S. Application Data

(63) Continuation of application No. PCT/CN2018/110087, filed on Oct. 12, 2018.

(30) Foreign Application Priority Data

Apr. 28, 2018    (CN) .......................... 201810397714.9

(51) Int. Cl.
    *A61K 35/741*      (2015.01)
    *C12N 1/20*      (2006.01)

(52) U.S. Cl.
    CPC .............. *A61K 35/741* (2013.01); *C12N 1/20* (2013.01)

(58) Field of Classification Search
    CPC ................................ A61K 35/741; C12N 1/20
    See application file for complete search history.

(56) References Cited

FOREIGN PATENT DOCUMENTS

| CN | 102947441 A | | 2/2013 |
|---|---|---|---|
| CN | 104546932 A | * | 4/2015 |
| CN | 104546932 A | | 4/2015 |
| CN | 106620189 A | | 5/2017 |

OTHER PUBLICATIONS

Lorenz, W., Buhrmann, C., Mobasheri, A., Lueders, C., & Shakibaei, M. (2013). Bacterial lipopolysaccharides form procollagen-endotoxin complexes that trigger cartilage inflammation and degeneration: implications for the development of rheumatoid arthritis. Arthritis research & therapy, 15(5), 1-17 (Year: 2013).*
Tan H, Yu Z, Wang C, Zhang Q, Zhao J, Zhang H, Zhai Q, Chen W. Pilot Safety Evaluation of a Novel Strain of Bacteroides ovatus. Front Genet. Nov. 6, 2018;9:539. doi: 10.3389/fgene.2018.00539. PMID: 30459813; PMCID: PMC6232662. (Year: 2018).*
Yang, C., Mogno, I., Contijoch, E. J., Borgerding, J. N., Aggarwala, V., Li, Z., . . . & Faith, J. J. (2020). Fecal IgA levels are determined by strain-level differences in bacteroides ovatus and are modifiable by gut microbiota manipulation. Cell host & microbe, 27(3), 467-475. (Year: 2020).*
Chen, Wei New Progress of Research On Gut Microbiota and Human Health, Journal of Chinese Institute of Food Science and Technology vol. 2, No. (17), Feb. 28, 2017 (Feb. 28, 2017).

* cited by examiner

*Primary Examiner* — Louise W Humphrey
*Assistant Examiner* — Trevor L Kane
(74) *Attorney, Agent, or Firm* — IPro, PLLC (57) ABSTRACT

The disclosure discloses *Bacteroides ovatus* for relieving endotoxin infection and application thereof, and belongs to the technical field of microorganisms. The *Bacteroides ovatus* CCFM1021 of the disclosure has low immunogenicity, and can reduce the content of pro-inflammatory factors and increase the concentration of anti-inflammatory factors in the blood of mice infected with endotoxin, up-regulate the number of Foxp3$^+$ regulatory T cells and stabilize the composition of the intestinal microbiota. A pharmaceutical composition of the *Bacteroides ovatus* CCFM1021 for relieving endotoxin infection has broad application prospects.

8 Claims, 5 Drawing Sheets

BACTEROIDES OVATUS FOR RELIEVING ENDOTOXIN INFECTION AND APPLICATION THEREOF

TECHNICAL FIELD

The disclosure relates to *Bacteroides ovatus* for relieving endotoxin infection and application thereof, and belongs to the technical field of microorganisms.

BACKGROUND

Mammalian intestine contains a large number of commensal bacteria, and the intestinal mucosa can selectively absorb nutrients and prevent the entry of microorganisms and their harmful metabolites. Endotoxin is one of the important components of the cell wall of Gram-negative bacteria, with stable structure. Only long-term high-temperature treatment or assisted by strong alkali, acid or oxidant can destroy the biological activity of endotoxin. Endotoxin is mainly composed of polysaccharide 0 antigen, core polysaccharide and lipid A.

Endotoxin is mainly responsible for the septic shock caused by Gram-negative bacteria, and can increase the intestinal permeability, act on the macrophages, neutrophils, endothelial cells, platelets as well as the complement system, the coagulation system by entering the blood circulation through the barrier, trigger systemic inflammatory response syndrome, lead to a series of intestinal diseases and multiple organ dysfunctions, and is likely to aggravate depression.

At present, the treatment principle for endotoxin infection is still based on bactericidal methods. For example, polymyxin can specifically bind the lipid A which is the active site of endotoxin, and thereby neutralizing or inactivating the toxicity. However, the release of endotoxin accompanied by bacteria death and lysis lead to the enhancement of damage to the body.

Therefore, to regulate the intestinal microbiota has broad application prospects in the treatment or prevention of endotoxin infection. However, there has no patent literature that reports the effect of *Bacteroides ovatus* on relieving endotoxin infection at present.

SUMMARY

The disclosure provides a novel strain of *Bacteroides ovatus*. The bacteria is identified as *Bacteroides ovatus* CCFM1021 according to the gene sequence, and has been preserved at the Guangdong Microbial Culture Collection Centeron Mar. 29, 2018, with the preservation address of 5th Floor, Building 59, Courtyard 100, Xianlie Middle Road, Guangzhou, and the preservation number of GDMCC No: 60343.

The *Bacteroides ovatus* CCFM1021 used the original number ELH-B2 before being submitted to the Guangdong Microbial Culture Collection Center.

The *Bacteroides ovatus* CCFM1021 has the following properties:

1) having low immunogenicity and no significant effect on immune factors in the blood and colon tissues of mice;

2) being capable of reducing the content of pro-inflammatory factors and increasing the concentration of anti-inflammatory factors in the blood of mice infected with endotoxin;

3) being capable of up-regulating the number of Foxp3$^+$ regulatory T cells in the spleen of mice infected with endotoxin; and 4) being capable of stabilizing the intestinal microbiota composition of mice infected with endotoxin.

Bacteria characteristics: the bacteria are Gram-negative and rod-shaped, are about 0.9-1.2 µm wide and 3-8 µm long, and have no sporulation.

Bacterial colony characteristics: obvious colonies are formed on a culture medium with the diameter of 0.5-1.0 mm; the front morphology is oval; the side morphology is convex; the edges are neat; the colonies are translucent; and the surface is moist and smooth.

Growth characteristics: the strain is strictly anaerobic, is sensitive to oxygen, and can grow nicely under at the temperature of 30-37° C. and the pH between 8.0 and 5.0. The most suitable pH for growth is 7.0.

The disclosure further provides application of the *Bacteroides ovatus* CCFM1021 in preparing a pharmaceutical composition for relieving endotoxin infection.

In one embodiment, the composition contains the *Bacteroides ovatus* CCFM1021, and further contains a cytoprotective agent.

In one embodiment, the cytoprotective agent includes but is not limited to a phosphate buffer solution.

In one embodiment, the pharmaceutical composition is composed of a *Bacteroides ovatus* CCFM1021 bacterial agent and pharmaceutically acceptable carriers.

In one embodiment, the amount of the *Bacteroides ovatus* CCFM1021 bacterial agent in the pharmaceutical composition is 15-35% or 20-30% by weight.

In one embodiment, the pharmaceutically acceptable carriers include one or more carriers selected from those commonly used in pharmacy as fillers, binders, wetting agents, disintegrants, lubricants and flavoring agents.

In one embodiment, the pharmaceutical composition can be presented in the form of granules, capsules, tablets, pills or oral liquid.

In one embodiment, the fillers refer to excipient diluents used for increasing the weight and volume of tablets to facilitate compressing, or excipient absorbents for absorbing excess liquid components in the raw materials. The filler s can be selected from starch, sucrose, lactose, calcium sulfate or microcrystalline cellulose.

In one embodiment, the binders refer to viscous substances that can be added when the drug has no viscosity or insufficient viscosity so as to facilitate granulation. The binders can be selected from cellulose derivatives, alginate, gelatin or polyvinylpyrrolidone.

In one embodiment, the wetting agents refer to liquid that can be added when the drug has no viscosity, so as to wet the the raw materials and excipients of the drug to induce the viscosity and form granules. The wetting agents can be selected from water, ethanol, starch or syrup.

In one embodiment, the disintegrants refer to excipients that can be added to tablets to promote rapid disintegration into fine particles in the gastrointestinal fluid. The disintegrants can be selected from sodium carboxymethyl starch, hydroxypropyl cellulose, croscarmellose, agar, calcium carbonate or sodium bicarbonate.

In one embodiment, the lubricant s refer to chemical substances that can improve the mobility of tablets during processing and demoulding. The lubricants can be selected from talc, calcium stearate, magnesium stearate, superfine silica gel powder or polyethylene glycol.

In one embodiment, the flavoring agents refer to excipients used in drugs to improve or shield the undesirable smell and taste. The flavoring agents can be selected from sweeteners such as simple syrup, sucrose, lecithin, orange syrup or cherry syrup; aromatics such as lemon, fennel or peppermint oil; mucilage agents such as sodium alginate, gum arabic, gelatin, methyl cellulose or sodium carboxymethyl cellulose; and effervescing agents such as citric acid, tartaric acid or a mixture of sodium bicarbonate.

The disclosure further provides a bacterial agent containing the *Bacteroides ovatus* CCFM1021 and cytoprotective agents.

In one embodiment, the cytoprotective agent includes a sodium alginate solution.

In one embodiment, the cytoprotective agent includes starch, cellulose derivatives, sodium carboxymethyl starch, talc, a sucrose water solution or a mixture thereof.

In one embodiment, the bacterial agent is powder obtained by preparing bacterial liquid containing the *Bacteroides ovatus* CCFM1021 through a conventional freeze-drying process or other processes, and contains active *Bacteroides ovatus* CCFM1021 with the content of $10^6$ CFU/g or above.

The disclosure further provides a cryopreserved agent of *Bacteroides ovatus*, containing the *Bacteroides ovatus* CCFM1021 with the content of greater than or equal to $10^{10}$ CFU/mL.

In one embodiment, the cryopreserved agent is prepared by inoculating *Bacteroides ovatus* CCFM1021 in culture medium, allowing to grow till stationary phase, followed by washing with a phosphate buffer solution of pH 7.0-7.2 for 1-2 times, adding protective agents and preserving at −80° C. for later use.

In one embodiment, the protective agent contains cysteine hydrochloride (1 g/L) and glycerin (200 g/L).

The disclosure further provides a method for culturing the *Bacteroides ovatus* CCFM1021, including inoculating the *Bacteroides ovatus* CCFM1021 into culture medium and anaerobically culturing at 35-37° C.

In one embodiment, the strain is cultured for 12-18 h to reach a stationary phase.

In one embodiment, BHI culture medium is used for culture.

In one embodiment, cysteine hydrochloride (1 g/L), hemin (0.01 g/L), and vitamin K1 (0.002 g/L) are also added to the BHI culture medium.

The disclosure further provides application of the *Bacteroides ovatus* CCFM1021 in relieving endotoxin infection, and the application is to ingest the *Bacteroides ovatus* or a composition containing the *Bacteroides ovatus* into the body.

In one embodiment, the *Bacteroides ovatus* is ingested into the body in the form of a pharmaceutical composition.

Beneficial effects: The *Bacteroides ovatus* CCFM1021 of the disclosure has low immunogenicity, can significantly improve the serum content of inflammatory factors and the number of Foxp3$^+$ regulatory T cells in the spleen of the mice infected with endotoxin infection to the level of normal mice, and can stabilize the composition of the intestinal microbiota of mice infected with endotoxin. The *Bacteroides ovatus* CCFM1021 can be used to prepare a pharmaceutical composition that are capable of relieving endotoxin infection, and has broad application prospects.

PRESERVATION PROOF OF THE BIOLOGICAL MATERIALS

A novel *Bacteroides* strain, with a taxonomic name of *Bacteroides ovatus*, has been preserved at the Guangdong Microbial Culture Collection Centeron Mar. 29, 2018, with the preservation address of 5th Floor, Building 59, Courtyard 100, Xianlie Middle Road, Guangzhou, and the preservation number of GDMCC No: 60343. The *Bacteroides ovatus* CCFM1021 used the original number ELH-B2 before being submitted to the Guangdong Microbial Culture Collection Center, and therefore, the numbers CCFM1021 and ELH-B2 represent the same strain of *Bacteroides ovatus*.

DETAILED DESCRIPTION

Example 1: Culture and Preservation Method of *Bacteroides ovatus* CCFM1021

Preparation of a culture medium: brain heart infusion BHI culture medium (such as a product of Qingdao Haibo Biotechnology Co., Ltd.) was weighed proportionally and dissolved in distilled water. Cysteine hydrochloride (1 g/L), hemin (0.01 g/L) and vitamin K1 (0.002 g/L) were added and mixed uniformly. The pH was adjusted to 7.0, and sterilization was carried out at 115-121° C. for 15-20 min to obtain the culture medium.

Culture method: *Bacteroides ovatus* CCFM1021 strain was inoculated according to an inoculation amount of 2-4% based on the weight of the above culture medium, and anaerobically cultured at 37° C. for 12-18 h to reach a stationary phase.

Preparation of protective agent: cysteine hydrochloride (1 g/L) and glycerol (200 g/L) were weighed and uniformly dissolved in distilled water, and the mixed solution was sterilized at 115-121° C. for 15-20 min to obtain the protective agent.

Preservation method: liquid culture of *Bacteroides ovatus* CCFM1021 in the stationary phase was washed with a sterile phosphate buffer solution (pH 7.2) for 1-2 times, and then resuspend with the prepared protective agent to reach the concentration of $10^{10}$ CFU/mL, so as to obtain the *Bacteroides ovatus* CCFM1021 cryopreserved agent, and the *Bacteroides ovatus* CCFM1021 cryopreserved agent was preserved at −80° C. for later use.

Example 2: Tolerance Dose Experiment in Mice with Intragastric Administration of

*Bacteroides ovatus* CCFM1021

10 of 6-8 week old healthy female C57BL6 mice were taken and intragastrically administered with 0.1 mL of the cryopreserved agent containing *Bacteroides ovatus* CCFM1021 ($10^{10}$ CFU/mL) prepared as Example 1 once every 24 hours. The mice were observed for 5 days and the body weight and death of the mice were recorded.

Experimental results are listed in Table 1. These results showed that feeding the *Bacteroides ovatus* CCFM1021 at the concentration of $10^9$ CFU did not cause any negative effects on the mice. The mice grew normally, no death occurred, and the mice had no pathological symptoms.

TABLE 1

Influence of $10^9$ CFU of *Bacteroides ovatus* CCFM1021 on body weight of mice

| Time (d) | 1 | 2 | 3 | 4 | 5 |
|---|---|---|---|---|---|
| Body weight (g) | 20.76 ± 0.71 | 21.25 ± 0.63 | 21.42 ± 0.37 | 21.79 ± 0.83 | 22.13 ± 1.02 |
| Death | None | None | None | None | None |

Example 3: Immune Tolerance Experiment in Mice with Intragastric Administration of *Bacteroides ovatus* CCFM1021

20 of 6-8 week old healthy female C57BL6 mice were randomly divided into two groups: a negative control group and a *Bacteroides ovatus* CCFM1021 intervention group, each group contained 10 mice. Mice in the *Bacteroides ovatus* CCFM1021 intervention group were intragastrically administered with 0.1 mL of the above *Bacteroides ovatus* CCFM1021 cryopreserved agent ($10^{10}$ CFU/mL) once every 24 hours, while mice in the control group were intragastrically administered with 0.1 mL of the protective agent of the above cryopreserved agent once every 24 hours. All mice were sacrificed after 5 days of continuous intragastric administration. After blood and colon tissue were taken, lysed and homogenized with RIPA lysate (a product of Beyotime Biotechnology Co., Ltd.), the concentration of immune factors was determined with an ELISA kit (a product of Nanjing SenBeiJia Biological Technology Co., Ltd.).

Figure 1:
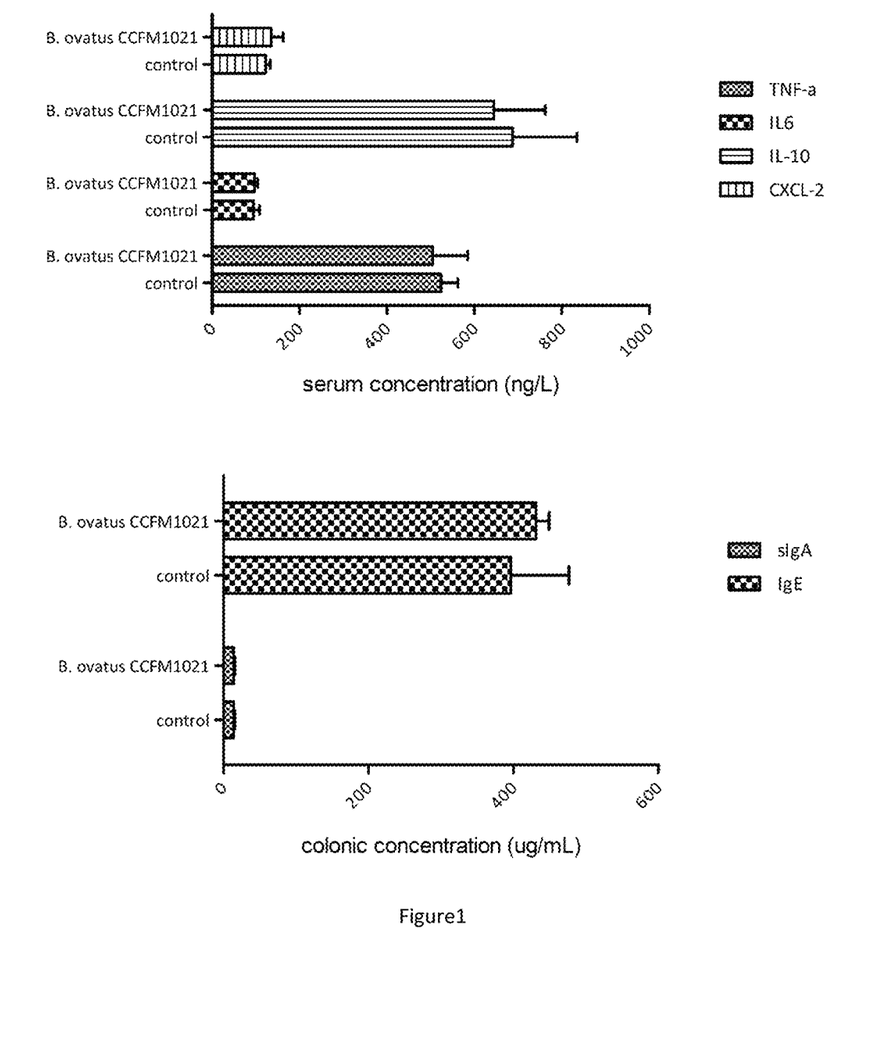
FIG. 1 shows the concentration of immune factors in the blood and colon tissue of mice after intragastric administration of *Bacteroides ovatus* CCFM1021.

Experimental results are shown in FIG. 1, which indicated that the contents of the immune factors of TNF-α, IL-6, IL-10 and CXCL-2 in the blood and the immune factors of sIgA and IgE in the colon tissue of mice in the *Bacteroides ovatus* CCFM1021 intervention group were not significantly different from those of mice in the control group. Therefore, the results of Example 3 show that *Bacteroides ovatus* CCFM1021 of the disclosure does not stimulate the immune system of mice and has low immunogenicity.

Example 4: Regulating Effects of *Bacteroides ovatus* CCFM1021 on the Level of Immune Factors in the Blood of Mice Infected with Endotoxin 30 of 6-8 week old healthy female C57BL6 mice were randomly divided into three groups: a negative control group, an endotoxin infection model group and a *Bacteroides ovatus* CCFM1021 treatment group, each group contained 10 mice. Mice in the endotoxin infection group and the *Bacteroides ovatus* CCFM1021 treatment group were intraperitoneally injected with 0.1 mL of an endotoxin solution (0.1 mg/kg) diluted with normal saline once every 24 hours. Mice in the control group and the endotoxin infection group were intragastrically administered with 0.1 mL of the protective agent of the cryopreserved agent once every 24 hours. The mice in the *Bacteroides ovatus* CCFM1021 treatment group were intragastrically administered with 0.1 mL of the *Bacteroides ovatus* CCFM1021 cryopreserved agent ($10^{10}$ CFU/mL) once every 24 hours. All mice were sacrificed after 5 consecutive days. Blood was collected and the concentration of immune factors was determined by using an ELISA kit (a product of Nanjing SenBeiJia Biological Technology Co., Ltd.).

Figure 2:
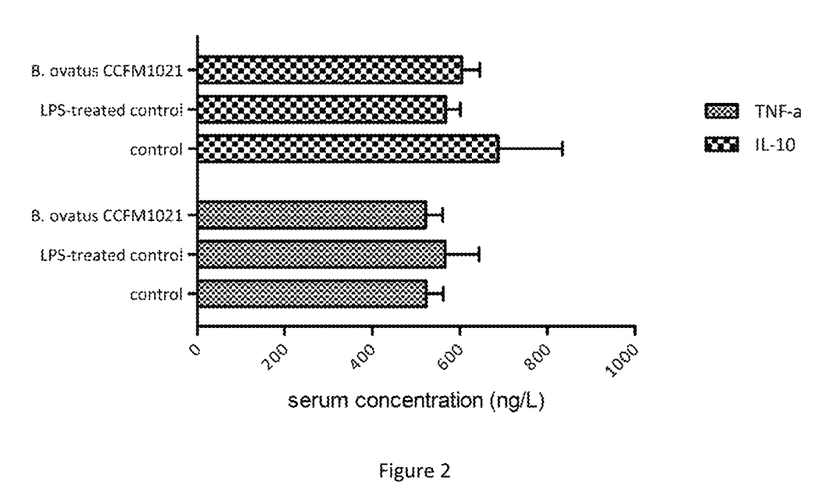
FIG. 2 shows the regulating effects of *Bacteroides ovatus* CCFM1021 on the level of immune factors in the blood of mice infected with endotoxin.

Experimental results are shown in FIG. 2, which indicated that endotoxin infection increased the content of the pro-inflammatory factor TNF-α in the blood of mice from 522.93 ng/L to 566 ng/L, while decreased the anti-inflammatory factor IL-10 from 686.83 ng/L to 567.68 ng/L. After treatment with *Bacteroides ovatus* CCFM1021, the content of TNF-α in the blood of mice was down-regulated to 521 ng/L, and the content of IL-10 was up-regulated to 604 ng/L, making the levels of the above immune factors close to those of the mice in the control group. Therefore, the results of Example 4 indicate that *Bacteroides ovatus* CCFM1021 of the disclosure can relieve the inflammatory response caused by endotoxin infection.

Example 5: Regulating Effects of *Bacteroides ovatus* CCFM1021 on the Level of Regulatory T Cells in the Spleen of Mice Infected with Endotoxin 30 of 6-8 week old healthy female C57BL6 mice were randomly divided into three groups: a negative control group, an endotoxin infection model group and a *Bacteroides ovatus* CCFM1021 treatment group, each group contained 10 mice. Mice in the endotoxin infection group and the *Bacteroides ovatus* CCFM1021 treatment group were intraperitoneally injected with 0.1 mL of an endotoxin solution (0.1 mg/kg) diluted with normal saline once every 24 hours. Mice in the control group and the endotoxin infection group were intragastrically administered with 0.1 mL of the protective agent of the cryopreserved agent once every 24 hours. The mice in the *Bacteroides ovatus* CCFM1021 treatment group were intragastrically administered with 0.1 mL of the *Bacteroides ovatus* CCFM1021 cryopreserved agent ($10^{10}$ CFU/mL) once every 24 hours. All mice were sacrificed after 5 consecutive days. After the spleen tissue was taken, lysed and homogenized with red blood cell lysate, CD4, CD25 and surface molecule Foxp3 were labeled by using a mouse regulatory T cell staining kit (a product of eBioscience company), and the content change of the regulatory T cells was detected by flow cytometry (FACSCalibur, BD company).

Figure 3:
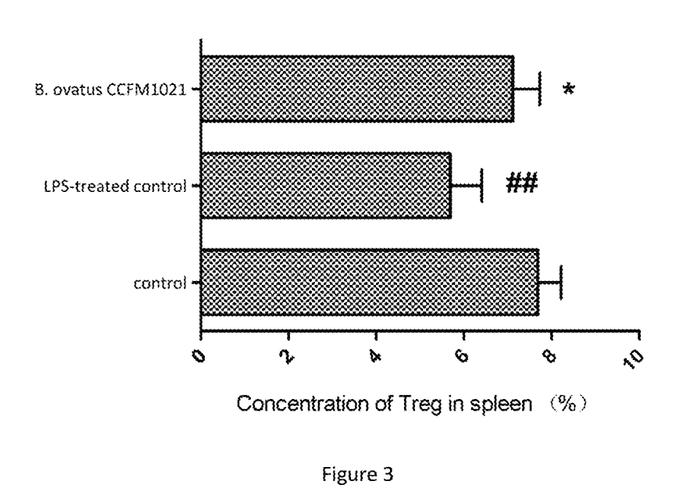
FIG. 3 shows the regulating effects of *Bacteroides ovatus* CCFM1021 on the level of regulatory T cells in the spleen of mice infected with endotoxin; * indicates that there is a significant difference between the *Bacteroides ovatus* CCFM1021 group and the endotoxin model group, and * indicates p<0.05; # indicates that there is a significant difference between the endotoxin infection group and the control group, and ## indicates p<0.01.
Figure 4:
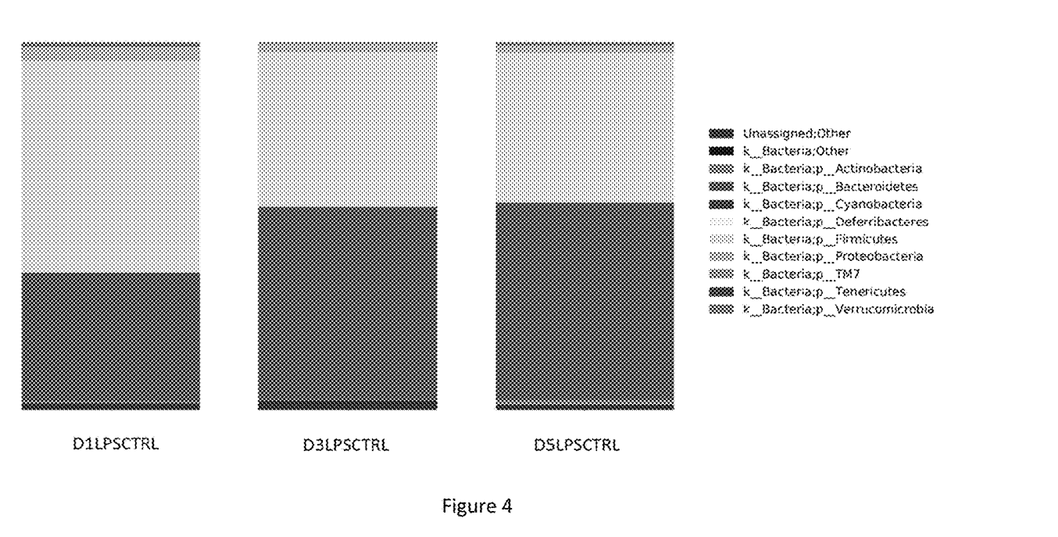
FIG. 4 shows the intestinal microbiota of mice in the endotoxin infection group; D1LPSCTRL: the intestinal microbiota of mice in the endotoxin infection group on the 1st day of the experiment; D3LPSCTRL: the intestinal microbiota of mice in the endotoxin infection group on the 3rd day of the experiment; and D5LPSCTRL: the intestinal microbiota of the mice in the endotoxin infection group on the 5th day of the experiment.
Figure 5:
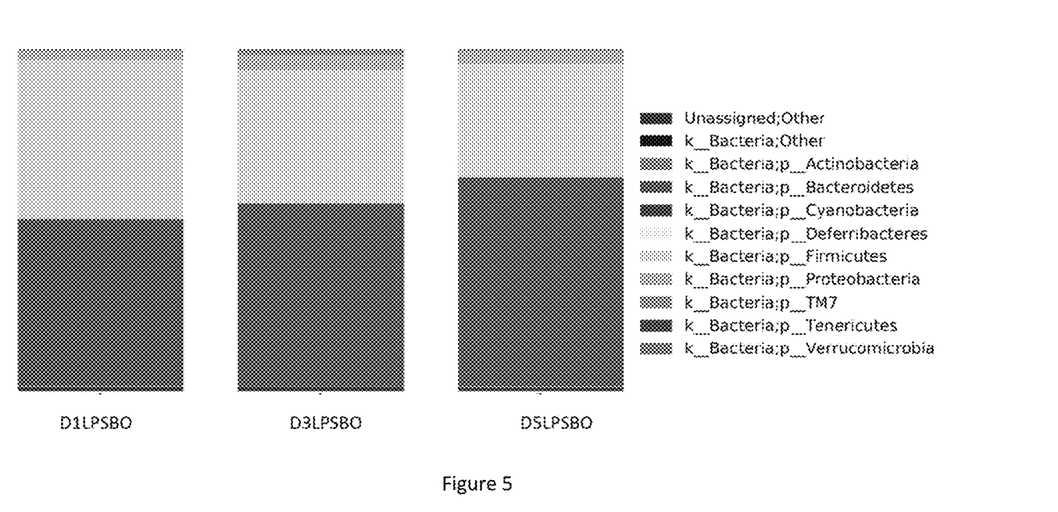
FIG. 5 shows the regulating effects of *Bacteroides ovatus* CCFM1021 on the composition of the intestinal microbiota of mice infected with endotoxin; D1LPSBO: the intestinal microbiota of mice in the endotoxin infection group with the intervention of *Bacteroides ovatus* CCFM1021 on the 1st day of the experiment; D3LPSBO: the intestinal microbiota of mice in the endotoxin infection group with the intervention of *Bacteroides ovatus* CCFM1021 on the 3rd day of the experiment; and D5LPSBO: the intestinal microbiota of mice in the endotoxin infection group with the intervention of *Bacteroides ovatus* CCFM1021 on the 5th day of the experiment.
Figure 6:
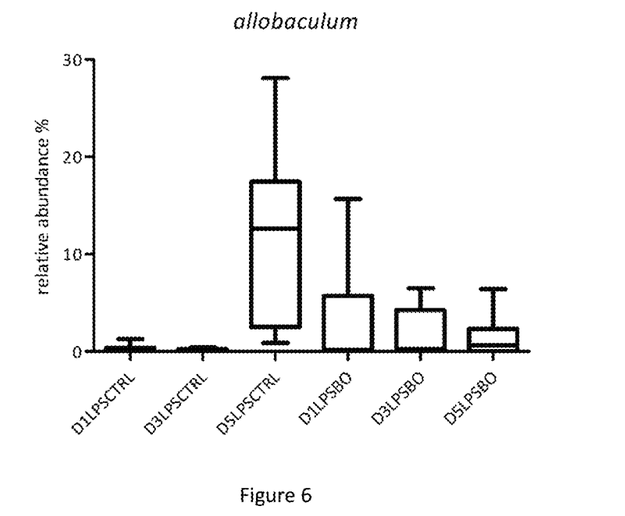
FIG. 6 shows the relative abundance of Allobaculum in the intestinal microbiota of mice infected with endotoxin and in the intestinal microbiota of mice in the endotoxin infection group with the intervention of *Bacteroides ovatus* CCFM1021.
Figure 7:
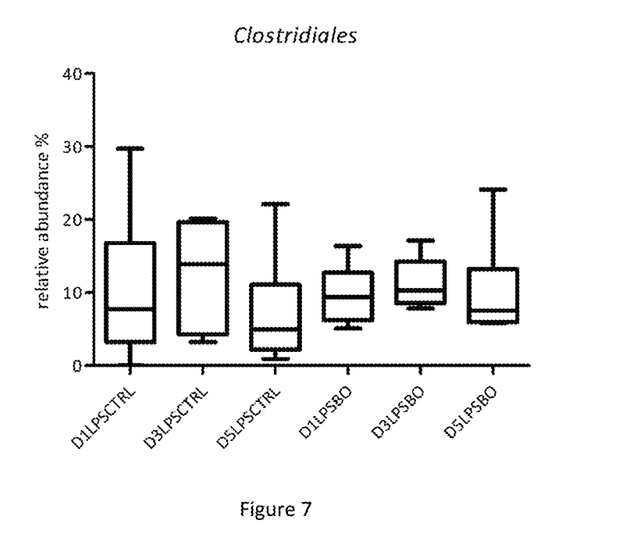
FIG. 7 shows the relative abundance of Clostridiales in the intestinal microbiota of mice infected with endotoxin and in the intestinal microbiota of mice in the endotoxin infection group with the intervention of *Bacteroides ovatus* CCFM1021.
Figure 8:
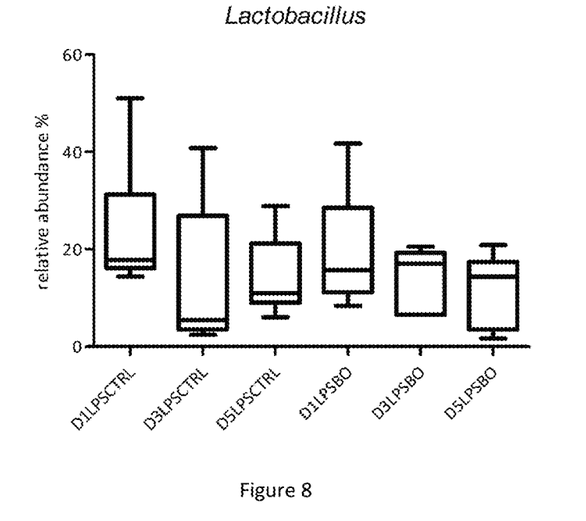
FIG. 8 shows the relative abundance of *Lactobacillus* in the intestinal microbiota of mice infected with endotoxin and in the intestinal microbiota of mice in the endotoxin infection group with the intervention of *Bacteroides ovatus* CCFM1021.

Experimental results are shown in FIG. 3, which indicated that endotoxin infection significantly reduced the Foxp3$^+$ regulatory T cells in the spleen of mice from 7.69% to 5.69% ($p<0.01$). After treatment with *Bacteroides ovatus* CCFM1021, the content of the regulatory T cells in the spleen of mice increased significantly to 7.12% ($p<0.05$), which was close to the level of mice in the control group. The results of Example 5 indicate that the *Bacteroides ovatus* CCFM1021 of the disclosure can relieve the inflammatory response caused by endotoxin infection.

Example 6: Regulating Effects of *Bacteroides ovatus* CCFM1021 on the Composition of the Intestinal Microbiota of Mice Infected with Endotoxin 30 of 6-8 week old healthy female C57BL6 mice were randomly divided into three groups: a negative control group, an endotoxin infection model group and a *Bacteroides ovatus* CCFM1021 treatment group, each group contained 10 mice. Mice in the endotoxin infection group and the *Bacteroides ovatus* CCFM1021 treatment group were intraperitoneally injected with 0.1 mL of an endotoxin solution (0.1 mg/kg) diluted with normal saline once every 24 hours. Mice in the control group and the endotoxin infection group were intragastrically administered with 0.1 mL of the protective agent of the cryopreserved agent once every 24 hours. The mice in the *Bacteroides ovatus* CCFM1021 treatment group were intragastrically administered with 0.1 mL of the *Bacteroides ovatus* CCFM1021 cryopreserved agent ($10^{10}$ CFU/mL) once every 24 hours. All mice were sacrificed after 5 consecutive days. During the experiment, the mouse feces was taken before intragastric administration on the first day and after intragastric administration on the third day and the fifth day. After extracting the genomic DNA of fecal bacteria with a Fast DNA Spin Kit for Feces (a product of MP Biomedicals Company), the 16s V3-V4 region sequence was amplified by PCR, and the differences in the composition of the intestinal microbiota in the feces samples were determined by next-generation sequencing.

Experimental results are shown in FIGS. 4 to 8. The contents of *Bacteroides* and Firmicutes in the intestines of mice infected with endotoxin were 50% and 40% respectively, wherein *Bacteroides* S24-7 accounted for 42.7%, *Lactobacillus* accounted for 12%, Clostridiales accounted for 8.2%, and the content of Allobaculum related to colitis increased significantly to 10%, leading to a decrease in the diversity of intestinal microbiota. After treatment with *Bacteroides ovatus* CCFM1021, it was found that the abundance of Bacteroidetes and Firmicutes in the fecal flora of mice were adjusted to 60% and 30%, wherein *Bacteroides* S24-7 maintained at 43%. The variations of Clostridiales and Allobaculum were greatly reduced, the abundance of which was 9.8% and 1.7% respectively, and the content of *Lactobacillus* increased to about 13.7%. Therefore, the results of Example 6 showed that the *Bacteroides ovatus* CCFM1021 of the disclosure can improve the disorders of the intestinal microbiota caused by LPS, increase the diversity of the intestinal microbiota and stabilize the balance of the intestinal microbiota, thereby prevent a series of diseases that may be caused by the imbalance of the intestinal microbiota caused by endotoxin.

The above examples showed that the *Bacteroides ovatus* CCFM1021 of the disclosure can help relieve the imbalance of the composition of the intestinal microbiota and the immune response caused by endotoxin infection in mice.

Example 7: Preparation of Capsule Products Containing *Bacteroides ovatus* CCFM1021 of the Disclosure The *Bacteroides ovatus* CCFM1021 of the disclosure was cultured anaerobically in BHI culture medium at 37° C. for 24 hours. The liquid culture was centrifuged at 5000 rpm for 15 min at 4° C., and washed 1-2 times with a sterile phosphate buffer solution (pH 7.2). The bacteria were resuspended using the above protective agent to make the final concentration of the bacteria reach $10^{10}$ CFU/mL. The bacterial suspension was added to sodium alginate solution, and mixed thoroughly to make cells evenly dispersed. Then the mixed solution was squeezed into a calcium chloride solution to form colloidal particles. After static solidification for 30 min, the colloidal particles were filtered and collected. The collected colloidal particles were freeze-dried for 48 hours to obtain powder containing the *Bacteroides ovatus* CCFM1021 of the disclosure. The powder was encapsulated with commercially available medicinal capsules to obtain the capsule product.

Example 8: Preparation of Tablets Using *Bacteroides ovatus* CCFM1021 of the Disclosure 25.7 parts by weight of the *Bacteroides ovatus* CCFM1021 bacterial powder preparation prepared by a freeze-drying method, 55.0 parts by weight of starch, 4.5 parts by weight of a cellulose derivative, 12.0 parts by weight of sodium carboxymethyl starch, 0.8 part by weight of talc, 1.0 part by weight of sucrose and 1.0 part by weight of water were individually weighed and mixed. The mixed material was made into wet granules by a conventional method, and then the wet granules were compressed with a tablet press produced by Zhongnan Pharmaceutical Machinery. The tablets were dried by a small medicine dryer produced by QingzhouYikang Traditional Chinese Medicine Machinery Co., Ltd., and then the tablets were packaged to obtain the tablets of the disclosure.

Although the disclosure has been disclosed as above in preferred examples, it is not intended to limit the disclosure. Without departing from the spirit and scope of the disclosure, anyone familiar with this technology can make various changes and modifications. Therefore, the protection scope of the disclosure should be defined by the claims.

What is claimed is:

1. A composition comprising: an active bacterium of *Bacteroides ovatus* with a preservation number of GDMCC No: 60343, preserved at the Guangdong Microbial Culture Collection Center (GDMCC) on Mar. 29, 2018, and an effective amount of a cryopreservation agent, and wherein the *Bacteroides ovatus* is present at a concentration of $10^6$ CFU/g or above in the composition.

2. The composition of claim 1, wherein the cryopreservation agent comprises a phosphate buffer solution and one or more protective agents comprising cysteine hydrochloride and glycerine.

3. The composition of claim 1, further comprising pharmaceutically acceptable carriers.

4. The composition of claim 3, wherein the *Bacteroides ovatus* is 15% to 35% by weight of the composition.

5. The composition of claim 3, wherein the pharmaceutically acceptable carriers are selected from: fillers, binders, wetting agents, disintegrants, lubricants, and flavoring agents.

6. The composition of claim 3, wherein the composition is in the form of granules, capsules, tablets, pills or oral liquid.

7. The composition of claim 5, wherein the fillers are excipient diluents or excipient absorbents.

8. A method of relieving endotoxin infection in a subject in need thereof, which comprises administering to the subject a composition comprising:

an active bacterium of *Bacteroides ovatus* with a preservation number of GDMCC No: 60343, preserved at the Guangdong Microbial Culture Collection Center (GDMCC) on Mar. 29, 2018 and a cryopreservation agent.

* * * * *